(12) United States Patent
Kapur

(10) Patent No.: US 11,331,421 B2
(45) Date of Patent: May 17, 2022

(54) EXPANDABLE ECMO EXTENSION CANNULA SYSTEM

(71) Applicant: Tufts Medical Center, Inc., Boston, MA (US)

(72) Inventor: Navin K. Kapur, Hanover, MA (US)

(73) Assignee: Tufts Medical Center, Inc., Boston, MA (US)

( * ) Notice: Subject to any disclaimer, the term of this patent is extended or adjusted under 35 U.S.C. 154(b) by 38 days.

(21) Appl. No.: 16/840,284

(22) Filed: Apr. 3, 2020

(65) Prior Publication Data
US 2021/0308359 A1 Oct. 7, 2021

(51) Int. Cl.
*A61M 1/36* (2006.01)
*A61M 25/00* (2006.01)
*A61M 39/06* (2006.01)

(52) U.S. Cl.
CPC ........ *A61M 1/3659* (2014.02); *A61M 1/3613* (2014.02); *A61M 25/0012* (2013.01); *A61M 39/06* (2013.01); *A61M 2025/0024* (2013.01); *A61M 2039/0633* (2013.01); *A61M 2210/127* (2013.01)

(58) Field of Classification Search
CPC ........ A61M 1/3659; A61M 2025/0031; A61M 2025/0024; A61M 25/04; A61M 2025/0004; A61M 2210/127
See application file for complete search history.

(56) References Cited

U.S. PATENT DOCUMENTS

| | | |
|---|---|---|
| 5,125,903 A | 6/1992 | McLaughlin et al. |
| 5,195,980 A | 3/1993 | Catlin |
| 5,269,764 A | 12/1993 | Vetter et al. |
| 6,083,198 A | 7/2000 | Afzal |
| 6,183,443 B1 | 2/2001 | Kratoska et al. |
| 6,210,365 B1 | 4/2001 | Afzal |
| 6,632,236 B2 | 10/2003 | Hogendijk |

(Continued)

OTHER PUBLICATIONS

Pavlushkov, et al., Cannulation techniques for extracorporeal life support. *Ann Transl Med.*, 5(4):70 (2017), doi:10.21037/atm.2016.11.47.

(Continued)

*Primary Examiner* — Emily L Schmidt
(74) *Attorney, Agent, or Firm* — Eversheds Sutherland (US) LLP; Nicola A. Pisano; Albert K. Heng

(57) ABSTRACT

An extension cannula and in-line connector for use with a conventional ECMO return cannula is provided. The extension cannula includes a self-expanding conduit transitionable between a collapsed insertion state and an expanded, deployed state via a retractable sheath. The extension cannula may be inserted through a conventional ECMO return cannula such that the proximal end of the self-expanding conduit is disposed within and proximal to the end of the conventional ECMO cannula, while the distal end of the self-expanding conduit is disposed in a patient's thoracic aorta to improve cerebral oxygenation, maintain systemic arterial pulsatility, and reduce the potential for end-organ injury. The extension cannula and/or in-line connector may be used to permit delivery of additional interventional or vascular equipment using a single port of access, thereby avoiding complications associated with contemporary VA-ECMO.

26 Claims, 14 Drawing Sheets

(56) References Cited

U.S. PATENT DOCUMENTS

| | | | |
|---|---|---|---|
| 7,938,809 | B2 | 5/2011 | Lampropoulos et al. |
| 8,996,095 | B2 | 3/2015 | Anderson et al. |
| 9,144,662 | B2 | 9/2015 | Dicaprio et al. |
| 10,485,956 | B2 | 11/2019 | O'Donovan |
| 2014/0012281 | A1* | 1/2014 | Wang ............... A61M 25/0023 606/108 |
| 2016/0158489 | A1* | 6/2016 | Wu .................... A61M 1/3659 604/509 |
| 2017/0080178 | A1 | 3/2017 | O'Connell et al. |
| 2017/0238951 | A1 | 8/2017 | Yang et al. |
| 2018/0193026 | A1* | 7/2018 | Yang ................. A61B 17/1214 |
| 2018/0207399 | A1* | 7/2018 | Chou ................ A61M 25/0052 |
| 2018/0243004 | A1* | 8/2018 | Von Segesser ..... A61M 1/3661 |
| 2019/0160259 | A1* | 5/2019 | Cottone ............. A61M 25/0113 |
| 2019/0247564 | A1 | 8/2019 | Lu et al. |
| 2019/0358434 | A1* | 11/2019 | Fuller ............... A61B 17/00234 |
| 2020/0146852 | A1* | 5/2020 | Raychev ................... A61F 2/90 |

OTHER PUBLICATIONS

Sulimov, M.D., et al., Rescue Peripheral Intervention Using A Peripheral ECMO-Cannula as Vascular Access, *J. Amm. Coll. Cardiol. Intv.*, Jan. 29, 2020, epublished DOI:10.1016/j.jcin.2019.11.038.

International Search Report & Written Opinion dated Sep. 13, 2021 in Int'l PCT Patent Appl. Serial No. PCT/US2021/025461.

* cited by examiner

EXPANDABLE ECMO EXTENSION CANNULA SYSTEM

FIELD OF THE INVENTION

This application relates generally to systems and methods for improving systemic perfusion and reducing complications during venous-arterial extracorporeal membrane oxygenation (VA-ECMO), and more specifically, for improving perfusion using an in-line connector and self-expanding extension cannula to deliver oxygenated blood directly to the thoracic aorta.

BACKGROUND

Arterial perfusion to every major organ system, including the heart, kidneys and brain, is determined by arterial pressure, blood flow, vascular tone, and intra-organ vascular resistance. When a patient experiences low arterial perfusion due to heart failure, cardiopulmonary failure, and cardiogenic or septic shock, venous-arterial extracorporeal membrane oxygenation (VA-ECMO) systems may be used to provide both circulatory and gas exchange support by augmenting the flow of oxygenated blood. See, e.g., Pavlushkov E, Berman M, Valchanov K. Cannulation techniques for extracorporeal life support. Ann Transl Med 2017; 5(4):70. doi: 10.21037/atm.2016.11.47. Specifically, VA-ECMO drains blood from the venous system, oxygenates this blood outside of the patient, and then delivers oxygenated blood back to the arterial system, e.g., via the femoral artery. VA-ECMO is most commonly performed via large-bore cannulas placed in the femoral vein and femoral artery (known as peripheral VA-ECMO). VA-ECMO is an established strategy for cardiopulmonary support.

Despite increasing utilization of VA-ECMO, with nearly 5,000 extracorporeal membrane oxygenation devices in use annually in the U.S. alone, in-hospital mortality remains around 60%. One explanation for these poor outcomes is that peripherally cannulated VA-ECMO may cause kidney injury, increase the risk of stroke, and promote cerebral ischemia, bleeding, and vascular injury. Further, more than one large-bore cannula may be required to achieve high flow rates needed for systemic perfusion with VA-ECMO. Cannula number and size are directly associated with increased risk of bleeding, vascular trauma, and acute limb ischemia. Finally, peripherally cannulated VA-ECMO may pressurize the entire aorta and increase pressure inside the heart, which increases fluid in the lungs thereby causing acute lung injury. To mitigate lung injury, concomitant devices such as intra-aortic balloon pumps and Impella® pumps (made available by AbioMed, Danvers, Mass.) may be used concomitantly with VA-ECMO and require additional vascular puncture. All of these complications are associated with increased mortality, long-term morbidity, length of stay in the hospital, and healthcare costs. New approaches to limit complications associated with VA-ECMO are required.

Studies indicate that VA-ECMO support may decrease kidney function and even cause acute kidney injury due to increased arterial pressure and loss of pulsatile flow to the kidney resulting from the high rates of blood flow localized to the outlet region of arterial outlet return cannulas with conventional VA-ECMO. Such injuries may in turn activate autoregulatory mechanisms of the kidneys. For example, high rates of non-pulsatile flow encountered with conventional VA-ECMO cannulas have been observed to increase vascular resistance, which in turn increases the workload of the kidneys and exacerbates oxygen consumption. Up to 70% of patients receiving VA-ECMO develop acute kidney injury, which is directly associated with mortality. Studies have further indicated that use of VA-ECMO may lead to a significant increase in arterial flow, as well as promote an increase in pressure within the organ itself, which in turn decreases flow in the renal vein. Thus, the net effect of VA-ECMO use, with conventional return cannulas, is an increase in pressure inside the organ, such that flow through the kidney is decreased. These physiological findings correlate with an increase in biomarkers of kidney injury, suggesting that one mechanism responsible for kidney injury may be related to pressure build-up inside the kidney and a net decrease of blood flow through the kidney.

Previously known efforts to reduce perfusion injury are known in the art. For example, U.S. Pat. No. 6,083,198 to Afzal describes a perfusion catheter having segmented flow regions, in which an arterial return catheter includes a series of apertures along its length to more evenly distribute blood within the aorta, including the aortic arch. One drawback of the system described in that patent, however, is that the inner catheter includes a reduced diameter than the outer catheter, thereby reducing flow rates to the distal-most portions of the catheter.

Recent studies also indicate that VA-ECMO use results in increased risk of stroke, e.g., acute ischemic stroke and hemorrhagic stroke. Because VA-ECMO induces retrograde blood flow in the femoral artery towards the aorta, the brain is the last major organ to receive oxygenated blood delivered via a conventional femoral artery cannula. Further, in patients exhibiting north-south syndrome, e.g., when compromised lung function results in ejection of deoxygenated blood from the left ventricle into the ascending aorta, differential hypoxia may occur as a result of VA-ECMO patients' dependence on retrograde flow to deliver oxygenated blood to the upper body. To mitigate this effect, physicians currently perform additional vascular punctures in the arteries or veins to place additional large-bore cannulas that increase the risk of complications.

Central VA-ECMO, in which oxygenated blood is delivered directly to a central location, e.g., via a surgical cut-down to the aortic arch, has been hypothesized to provide more oxygenated blood flow to the brain and thus reduce the risk of stroke. However, such cannulation, as described for example in U.S. Pat. No. 6,210,365 to Afzal, requires invasive surgery and involves additional potential complications. Another solution theorized would be to deliver oxygenated blood directly to the venous side of the patient via an ECMO cannula; however, this would require creating additional large-bore punctures in the patient's vasculature and may be further complicated by the already existing cannula residing in the venous circulation from the original VA-ECMO configuration. Additionally, placement of rigid cannulas from the peripheral artery into a central location in the thoracic aorta may be limited by the inability to navigate large bore cannulas through the iliofemoral bifurcation, tortuous aortas, or across calcified aortas with atheromatous material lining the aorta.

In view of the foregoing, it would be desirable to provide systems and methods for delivering oxygenated blood via VA-ECMO from a point of entry in the femoral artery to a more central location to the patient, e.g., the thoracic aorta, to supply oxygenated blood to the brain and induce antegrade flow to lower portions of the descending aorta. Such systems and methods may thus improve blood flow to the brain, preserve brain function, reduce the risk of ischemic stroke, and reduce blood flow rates and pressures that could induce kidney injury.

U.S. Pat. No. 8,996,095 to Anderson describes a coronary guide extension catheter having a push member and a distal tubular member, which is configured to be positioned in a coronary artery for use during percutaneous transluminal coronary angioplasty. The guide extension catheter described in that patent is designed to stabilize the distal end of a coronary guide catheter to prevent movement away from the patient's ostium due to beating of the heart during the interventional procedure. Similarly, U.S. Pat. No. 10,485,956 to O'Donovan describes a guide extension catheter having a groove in a push member and a distal shaft for guiding an interventional coronary device therethrough. Such coronary guide extension catheters are unsuitable for use as perfusion cannulas in VA-ECMO due to the small lumen diameters and resulting low blood flow rates that could be achieved. These coronary guide extension catheters are not meant to redirect blood flow, but rather to facilitate delivery of coronary equipment into distal portions of the coronary vasculature.

U.S. Pat. No. 6,632,236 to Hogendijk describes a self-expanding catheter for use in stent delivery, in which a catheter is transluminally inserted in a collapsed delivery state, and self-expands to an expanded deployed state upon removal of a delivery sheath. That patent describes a self-expanding anchor formed of a self-expanding wire weave having an elastomeric polymeric coating, and is configured to protect against embolization during vascular interventions. The concept described in Hogendijk is not meant to redirect blood flow, but rather to filter out elements in the blood stream. Similarly, U.S. Pat. No. 6,183,443 to Kratoska describes an expandable introducer sheath for percutaneously introducing intravascular angioplasty catheters. Such self-expanding catheters have not been contemplated for use with VA-ECMO systems for perfusing oxygenated blood.

In view of the disadvantages of the previously known ECMO perfusion catheters, it would be desirable to provide a device for use with an ECMO system that can enhance blood flow to the thoracic aorta and aortic arch, improve cerebral oxygenation, maintain systemic arterial pulsatility, and reduce the potential for perfusion injury to the kidneys using a single port of access, thereby avoiding bleeding and vascular injury associated with contemporary VA-ECMO.

It further would be desirable to provide a device for use with an ECMO system that avoids the small flow lumen sizes of previously known reperfusion catheters, thereby permitting enhanced blood flow rates to the ascending aorta and aortic arch, while maintaining or reducing the diameter of the vascular opening to the femoral artery required to introduce the return cannula.

In contemporary practice, VA-ECMO is also used to support commonly performed life-saving procedures such as coronary angioplasty, aortic valvuloplasty, or aortic valve replacement. However, a major limitation of these approaches is the need for additional vascular access to place vascular sheaths and/or catheters for required interventional equipment in addition to the existing VA-ECMO circuit. This can be prohibitive for patients who have peripheral vascular disease, concomitant vascular injury, or vessels occupied by other life-saving equipment. Further, under emergent conditions, placing additional vascular access can be challenging and increase risk of injury.

U.S. Pat. Nos. 5,125,903, 5,195,980, 5,269,764, 7,938,809 describe percutaneous catheter introducers/connectors having hemostatic valves for permitting passage of elongated interventional devices into a patient's vasculature, and a side port for connection with, e.g., an outside source of perfusion, aspiration, contrast media, medicaments, etc. These systems are not designed for use with VA-ECMO. Moreover, no existing approach allows for simple and effective access to the VA-ECMO circuit for delivery of additional interventional equipment. Current Y-connectors used to provide access to an ECMO circuit suffer from numerous disadvantages including reduction in the effective lumen of the ECMO return cannula creating an undesirable pressure gradient, difficult angulations requirements that prohibit introduction of additional catheters without risk of kinking or catheter disruption. Such previously known connectors require the introducer sheath to be inserted nearly 25 to 30 cm more distal than usual due to interposition connecting tubing, thereby limiting access to the thoracic aorta, aortic root, aortic valve or coronary vasculature for therapeutic interventions. Such connectors also pose a risk of bleeding during ECMO disconnection and reconnection, with increased risk of air embolism and contamination due to disconnection from the ECMO circuit. See, e.g., Dmitriy S. Sulimov, MD et al., "Rescue Peripheral Intervention Using a Peripheral ECMO-Cannula as Vascular Access," J Am Coll Cardiol Intv. 2020 Jan. 29. Epublished DOI: 10.1016/j.jcin.2019.11.038.

It would therefore be desirable to provide a connector for providing simple and effective access to an ECMO circuit for delivery of interventional equipment.

SUMMARY OF THE INVENTION

In accordance with the principles of the present invention, devices and methods are provided for use with ECMO systems that overcome the disadvantages of the previously known ECMO reperfusion catheters. Specifically, devices constructed in accordance with the present invention enhance blood flow to the thoracic aorta, improve cerebral oxygenation, maintain systemic arterial pulsatility, reduce the potential for end-organ injury, and allow for delivery of additional interventional or vascular equipment using a single port of access, thereby avoiding bleeding and vascular injury associated with contemporary VA-ECMO.

In accordance with one aspect of the present invention, an extension cannula for use with a conventional ECMO return cannula is provided. The extension cannula includes an elongated shaft having a proximal end and a distal region, and a conduit coupled to the distal region of the elongated shaft. The elongated shaft may be used to position a proximal end in fluid communication with the lumen of the conventional ECMO return cannula, so that a distal end of conduit extends beyond the renal arteries, e.g., within the thoracic or abdominal aorta. The shaft may include a proximal end that extends through a port near a proximal end of the ECMO return cannula, where it may be manipulated by the clinician. The conduit has an inlet, an outlet, an internal lumen extending therebetween, and a diameter configured to transition between a collapsed insertion state and an expanded deployed state. The internal diameter of the conduit may be sized and shaped to receive at least one of a catheter for coronary, peripheral vascular, cerebral intervention, or valve intervention, a catheter for antegrade limb perfusion, or a catheter for delivery of intra-aortic, transvalvular pneumatic, or rotary flow pumps.

In a preferred embodiment, the conduit has a length selected so that when the extension cannula is inserted through a lumen of the conventional ECMO return cannula, the inlet of the conduit is in fluid communication with the outlet of the conventional ECMO return cannula and the outlet of the conduit extends beyond the renal arteries, and may reside in a patient's thoracic aorta, e.g., the descending aorta, the aortic arch, or the ascending aorta. In accordance with the principles of the present invention, as used herein, the patient's thoracic aorta may include the portion of the descending aorta above the level of the diaphragm such that the outlet of the conduit may reside in the descending aorta approaching the level of the diaphragm from beneath the patient's thoracic cavity. The conduit may include a support structure, such as a self-expanding mesh, weave or braid, encapsulated with a flexible biocompatible coating, e.g., ePTFE. Alternatively, the support structure may include a shape-memory alloy, plastic or stainless steel spine or skeleton. As a further alternative, the conduit may be take the form of a hollow sock structure having one or more pores coupled to a flexible spine. In this latter embodiment, the sock-like structure expands when filled with blood being ejected from the ECMO circuit.

The extension cannula of present invention is expected to provide improved delivery of oxygenated blood from the ECMO machine.

The extension cannula further may include a sheath sized and shaped to be removably disposed over the conduit to retain the conduit in the collapsed insertion state. Moreover, the support structure in a vicinity of the inlet of the conduit may include a feature that facilitates transition of the conduit to the collapsed insertion state when the sheath is advanced over the conduit. For example, the feature may include a tapered geometry of a proximal end of the support structure. Alternatively, the feature may include a plurality of support legs that couple a proximal end of the support structure to the elongated shaft.

In accordance with another aspect of the present invention, the inventive extension cannula may include an in-line connector having a first branch configured to be coupled to an outlet of an ECMO circuit, a second branch configured to permit insertion of the extension cannula, and an outlet configured to be coupled to the conventional ECMO return cannula. The first and second branches are in fluid communication with the outlet of the in-line connector, and the second branch preferably is co-linear with the outlet of the in-line connector. The in-line connector may be removably coupled to the conventional ECMO return cannula, or it may be incorporated into the conventional ECMO return cannula as a single unit.

A lumen extending from the second branch to the outlet of the in-line connector preferably is sized and shaped to receive at least one of the extension cannula, a catheter for coronary, peripheral vascular, cerebral, or valvular intervention, a catheter for antegrade limb perfusion, or a catheter for delivery of intra-aortic pneumatic, trans-valvular-axial-flow, or rotary-flow pumps. The in-line connector also may be used to provide wire re-access to the native femoral vessel, thereby allowing for removal of the ECMO cannula and delivery of vascular closure devices at the time of ECMO decannulation, thereby avoiding the need for surgical repair of the vessel. The inventive in-line connector also may include a side-arm for flushing of the in-line connector, which may be connected to an antegrade perfusion sheath to deliver oxygenated blood to protect against limb ischemia.

The second branch of the in-line connector may include a specially adapted hemostatic valve, either incorporated directly into the in-line connector or designed to couple to a standard ECMO cannula or tubing to facilitate cannula insertion, exchange, or removal. Preferably, the specially adapted hemostatic valve may be a stand-alone piece that may be incorporated into existing ECMO circuits.

In addition, the in-line connector may include an end cap configured to be coupled to an inlet of the second branch of the in-line connector. The end cap also may include a double hemostatic valve. Alternatively, the end cap may include a stopper sized and shaped to be received within a lumen of the second branch of the in-line connection, thereby preventing pooling of blood as oxygenated blood flows from the first branch to the outlet of the in-line connector. Additionally, the end cap may include a lumen sized and shaped to receive at least one of a drug infusion catheter or a pressure or flow sensor.

In accordance with yet another aspect of the present invention, the ECMO cannula may be configured to be positioned through a femoral vein, with the inlet of the extension cannula disposed within a patient's pulmonary artery, thereby serving as a cannula that selectively enables blood to be withdrawn from the pulmonary artery into the ECMO circuit. With this approach, it may be possible to reduce flow across the lung, thereby reducing left ventricle wall stress and distention, by decreasing preload to the left ventricle.

As a yet further alternative, the outlet of the extension cannula may be disposed in a patient's aortic root or left ventricle, and may be dimensioned to receive at least one of a catheter for coronary, peripheral, cerebral vascular or valvular interventions, or for placement of additional pump technologies within the left ventricle, such as a pneumatic or rotary flow pump inside the aorta, e.g., an intra-aortic balloon pump (IABPs), or trans-valvular rotary flow pump, e.g., Impella® pumps (made available by AbioMed, Danvers, Mass.).

In accordance with still another aspect of the invention, an extension cannula for use with an ECMO inlet cannula is provided having an inlet and an outlet. The extension cannula includes an elongated shaft having a proximal end and a distal region, and an expandable conduit coupled to the distal region of the elongated shaft. The conduit has an inlet, an outlet and an internal lumen, and has a diameter that transitions between a collapsed insertion state and an expanded deployed state. The conduit has a length selected so that when the extension cannula is inserted through a lumen of the ECMO inlet cannula, the outlet of the conduit is in fluid communication with the outlet of the ECMO inlet cannula and the inlet of the conduit resides in a patient's right ventricle.

Methods of using the extension cannula of the present invention also are provided.

In accordance with another aspect of the present invention, a valve is provided for use with an ECMO return cannula. The valve may include an end cap that may be fluidly coupled to an ECMO circuit. The end cap has a proximal end, a distal end that may be coupled to an ECMO return cannula, and a lumen extending therebetween. The lumen may be sized and shaped to receive at least one of an extension cannula, a catheter for coronary, peripheral vascular, cerebral, or valve intervention, a catheter for antegrade limb perfusion, or a catheter for delivery of intra-aortic, trans-valvular pneumatic or rotary flow pump, a drug infusion catheter, a pressure or flow sensor, or a replacement ECMO return cannula. Preferably, the specially adapted end-cap may be a stand-alone piece that may be incorporated into existing ECMO circuits. In a preferred embodiment, the valve includes a hemostatic valve disposed within the lumen of the end cap, such that the hemostatic valve permits uni-directional blood flow from the ECMO circuit to the ECMO return cannula. The proximal end of the end cap may be configured to be fluidly coupled to an ECMO circuit, while the distal end of the end cap may be coupled to the ECMO return cannula via an in-line connector as described above. The lumen of the end cap preferably is sized and shaped to permit removal of the ECMO return cannula and delivery of a second ECMO return cannula larger than the ECMO return cannula.

DETAILED DESCRIPTION OF THE INVENTION

Systems and methods are provided for use with ECMO systems to enhance blood flow to the thoracic aorta, ascending aorta and aortic arch, thereby facilitating normal antegrade flow to the carotid and other downstream arteries, while reducing high blood flow rates and the potential for reperfusion injury to the kidneys. The systems and methods of the present invention also may ameliorate the occurrence of north-south syndrome in patients with impaired lung function, thereby ensuring adequate flow of oxygenated blood to the patient's cerebral vasculature.

Figure 1A:
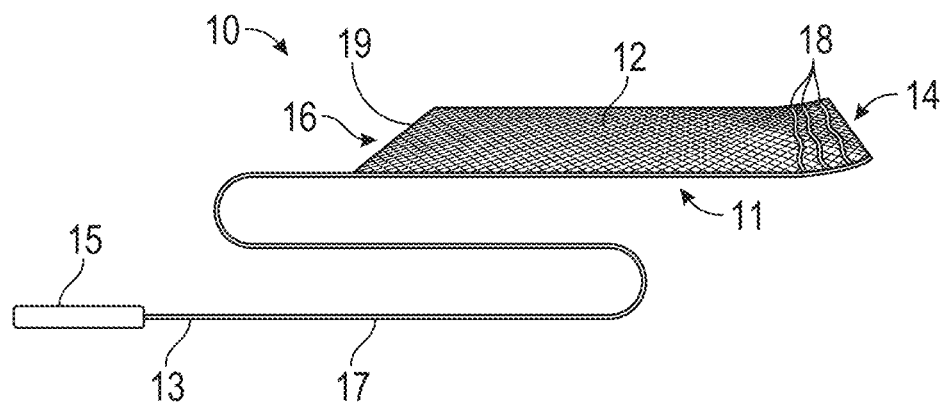
FIG. 1A is a side view of an extension cannula for improving reperfusion during ECMO, constructed in accordance with the principles of the present invention, with the extension conduit in an expanded state and with the delivery sheath removed.

Referring to FIG. 1A, extension cannula 10 suitable for use with a conventional VA-ECMO cannula is described. Extension cannula 10 includes shaft 17 extending between distal region 11 and proximal region 13 of extension cannula 10. Shaft 17 is formed of a material, e.g., stainless steel hypotube, having sufficient rigidity to permit cannula 10 to be advanced through a conventional ECMO reperfusion cannula so that distal region 11 of self-expanding conduit 12 may be disposed with its outlet extending beyond a patient's renal arteries, and preferably extending in a patient's ascending aorta or in the vicinity of the aortic arch. Self-expanding conduit 12 optionally may include handle 15 coupled to shaft 17 at proximal region 13 of self-expanding conduit 12 for maneuvering extension cannula 10.

Self-expanding conduit 12 has inlet 16 at its proximal end and outlet 14 at its distal end, and a lumen extending therethrough for permitting blood flow. Self-expanding conduit 12 has a length sufficient to extend from the outlet the conventional VA-ECMO cannula to a position above the patient's renal arteries, and more preferably, into the thoracic aorta, e.g., 30-120 cm. As described more fully below, self-expanding conduit 12 includes a self-expanding support structure, such as a mesh, weave or braid, covered by a flexible and biocompatible covering. Moreover, as shown in FIG. 1A, self-expanding conduit 12 may include one or more radiopaque markers 18 disposed along the distal end of self-expanding conduit 12 adjacent outlet 14 to permit its location to be determined fluoroscopically. In addition, the biocompatible covering in the vicinity of the distal end of self-expanding conduit 12 may be omitted to permit blood to exit laterally therethrough and perfuse the thoracic aorta.

Figure 1B:
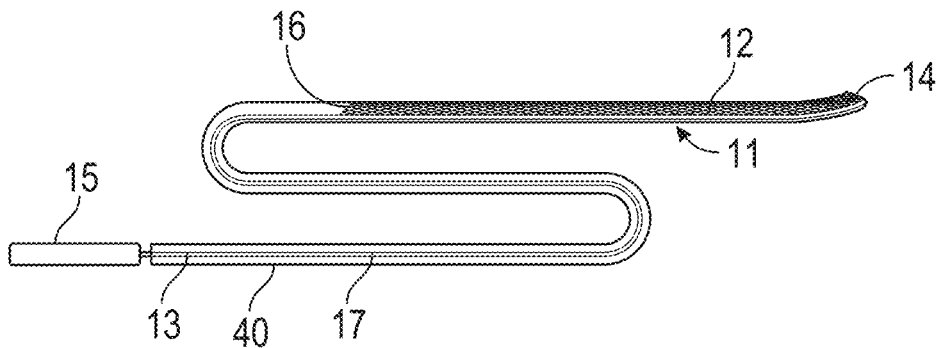
FIG. 1B is a side view of the extension cannula of FIG. 1A, with the extension conduit in a contracted state within the delivery sheath.

The support structure of self-expanding conduit 12 may be made of a wire mesh, weave or braid formed of a shape-memory metal or stainless steel, such that self-expanding conduit 12 may transition from a collapsed insertion state and an expanded deployed state. As depicted in FIG. 1B, the support structure of the conduit may be formed of a stainless steel mesh, weave or braid having a preset expanded diameter that forms a central lumen, such that the conduit may be contracted when pulled within smaller diameter delivery sheath 40. Alternatively, the support structure may be a mesh, weave or braid formed of a shape-memory metal such as a nickel-titanium alloy ("Nitinol"), and having a predetermined expanded diameter that forms the internal lumen. In this way, the conduit may be contracted to the collapsed insertion state when pulled within delivery sheath 40 as described in further detail below.

The support structure preferably is encapsulated with a biocompatible polymer coating, such as expanded polytetrafluoroethylene ("ePTFE"). In the expanded deployed state, self-expanding conduit 12 assumes a diameter substantially the same as, or even larger than, the internal lumen of a conventional VA-ECMO cannula, and thus does not require a larger-bore opening in the femoral vasculature. For example, the lumen of self-expanding conduit 12 may range from 15 Fr to 25 Fr in the expanded state. When inserted through a conventional ECMO cannula, self-expanding conduit 12 permits enhanced blood flow to the ascending aorta and aortic arch, while maintaining the diameter of the vascular opening in the femoral artery required to introduce the conventional VA-ECMO return cannula.

Still referring to FIG. 1A, in one preferred embodiment, inlet 16 at the proximal end of self-expanding conduit 12 may have a feature for facilitating recapture of self-expanding conduit 12 within the delivery sheath. For example, as shown in FIG. 1, self-expanding conduit 12 may have tapered geometry 19 that facilitates retrieval of self-expanding conduit 12. For example, the support structure of self-expanding conduit 12 may include a laterally displaced wire hoop that resides along the edge of inlet 16, thereby forming tapered geometry 19. Alternatively, the distal end of shaft 17 may be coupled to support legs coupled to the proximal end of the support structure of self-expanding conduit 12, such that advancing a sheath over the support legs causes the support structure of self-expanding conduit 12 to collapse inwardly to the collapsed insertion state as described in further detail below. In addition, the distal end of self-expanding conduit 12 may include an atraumatic region.

Figure 2:
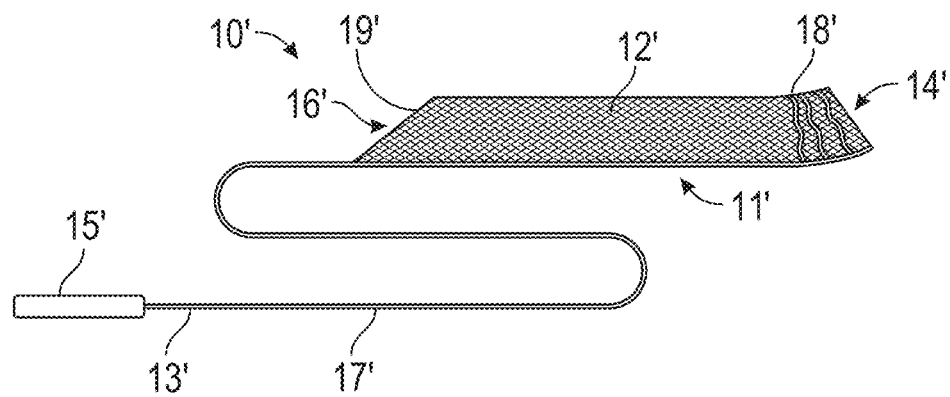
FIG. 2 is a side view of an alternative embodiment of the extension cannula of FIG. 1A, with the extension conduit in an expanded state and the delivery sheath removed.

Referring now to FIG. 2, alternative embodiment of extension cannula 10' of the present invention is described. In this embodiment, conduit 12' is made of a soft flexible material, such as polyethylene or nylon, and may include pores that permit some blood to perfuse laterally through the material while directing the bulk of the flow through conduit 12' to outlet 14'. Elongated shaft 17' serves as a spine to assist in passing extension conduit 12' through the lumen of a conventional ECMO cannula, and to position inlet 16' near the outlet of the ECMO cannula, and outlet 14' in distal region 11' above a patient's renal arteries, and more preferably, extending into the patient's thoracic aorta. Shaft 17' may be coupled to handle 15' for maneuvering device 10'. Conduit 12' preferably includes at its proximal end a self-expanding support hoop 19' that expands the opening 16' at proximal end of conduit 12' when released from a delivery sheath, as described above with respect to FIG. 1B. Conduit 12' may include radiopaque markers 18' near outlet 14'. Support hoop 19' ensures that blood flowing through the conventional ECMO cannula is funneled into the proximal end of conduit 12' and causes the remainder of conduit 12' to fully open. As for the embodiment of FIG. 1A, conduit 12' may be collapsed at the conclusion of a reperfusion procedure by advancing sheath 40 distally over elongated shaft 17' and conduit 12'.

Figure 3A:
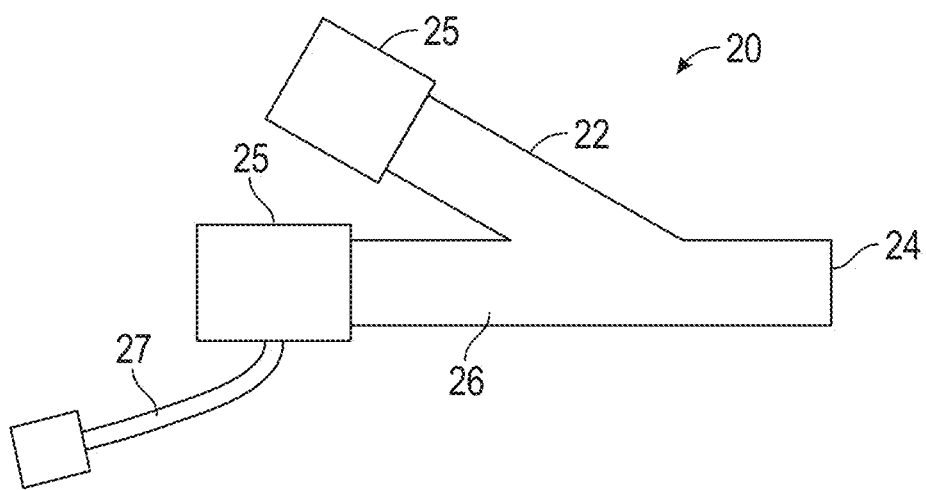
FIG. 3A is a schematic view of an exemplary in-line connector configured for use with the extension cannula of the present invention.

With respect to FIG. 3A, in-line connector 20 suitable for use with the extension cannula of the present invention is described. In-line connector 20 has first branch inlet 22 configured to be coupled to an outlet of a conventional ECMO machine for receiving oxygenated blood from an ECMO circuit, second branch inlet 26 having a hemostatic valve welded therein, and outlet 24 configured to be coupled to a conventional ECMO cannula. First branch inlet 22 and second branch inlet 26 each are in fluid communication with outlet 24, and each may include an optional hemostatic valve 25, as described below with respect to FIG. 3B. The fluid pathway extending between first branch inlet 22 and outlet 24 thus permits oxygenated blood received from an ECMO circuit to flow to through the conventional ECMO cannula and self-expanding conduit 12. Moreover, the fluid pathway extending between second branch inlet 26 and outlet 24 is sized and shaped to permit delivery therethrough of self-expanding conduit 12 in a collapsed insertion state, e.g., when disposed within delivery sheath 40. Accordingly, extension cannula 10 or 10' of FIGS. 1 and 2 may be inserted through the hemostatic valve of second branch inlet 26 and advanced through the lumen of the conventional ECMO return cannula coupled to outlet 24.

As will be understood by a person of ordinary skill in the art, the fluid pathway extending between second branch 26 and outlet 24 may be sized and shaped to permit delivery of other interventional tools therethrough as well, including, e.g., a catheter for coronary, peripheral, or cerebral vascular or valvular interventions, and/or a pneumatic, rotary, or transvalvular flow pump. Delivery of extension cannula 10 or 10' and other large-bore interventional devices or small catheters is possible due to co-linearity of second branch inlet 26 with outlet 24. Unlike previously known Y-shaped connectors used in interventional procedures, the linear alignment of second branch inlet 26 and outlet 24 of in-line connection 20 permits a device to be inserted without bending. Accordingly, the linear alignment of second branch inlet 26 and outlet 24 of in-line connector 20 accommodates delivery of large bore devices, e.g., a delivery catheter for a transcatheter aortic valve replacement (TAVR) valve, an Impella pump, or smaller catheters such as coronary, cerebral, or peripheral vascular interventional guide catheters.

In-line connector 20 may be removably coupled to the conventional ECMO return cannula when the extension cannula or other interventional devices are required to be delivered, e.g., by clamping the ECMO return cannula, decoupling the ECMO return cannula from the ECMO circuit, coupling in-line connector 20 to the ECMO circuit and the ECMO return cannula via first branch inlet 22 and outlet 24, respectively, and unclamping the ECMO return cannula. Alternatively, in-line connector 20 may be integrally constructed as part of the ECMO return cannula, e.g., a 15, 17, 19, 21, or 25 Fr conventional ECMO return cannula. Accordingly, in-line connector 20 may include an end cap coupled second branch inlet 26 when no device is delivered therethrough. As described above, second branch inlet 26 may include a hemostatic valve to prevent backflow of blood during delivery of the extension cannula or other interventional device, and the end cap may be coupled to second branch inlet 26 to prevent further exposure of the hemostatic valve.

Also shown in FIG. 3A is optional side arm 27 coupled to, and in fluid communication with, second branch inlet 26. Side arm 27 may be used for flushing of in-line connector 20 or may be used to fluidly couple in-line connector 20 to an antegrade perfusion catheter to perfuse the patient's lower extremities to protect against limb ischemia. For example, an antegrade perfusion catheter may be inserted via side arm 27, through in-line connector 20 and the convention ECMO return cannula, and positioned within the patient such that oxygenated blood is delivered to the patient's lower extremities.

Figure 3B:
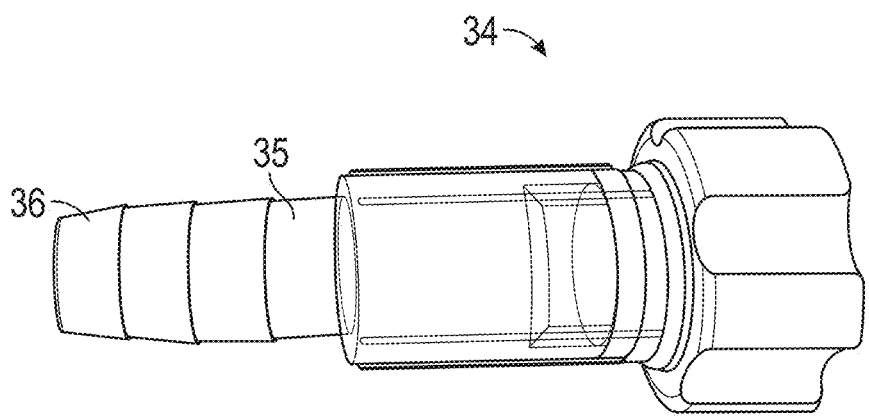
FIG. 3B illustrates an end cap for use with the in-line connector of FIG. 3A.

In accordance with another aspect of the invention, a variety of end caps and tubing adapters may be provided for use with second branch inlet 26 of in-line connector 20. For example, hemostatic valve 25 may have a diameter, e.g., a ⅜ inch, sized for selectively closing off second branch inlet 26 when not in use. Alternatively, an end cap may include a double hemostatic valve, as depicted in FIG. 3B, for preventing backflow of blood through second branch inlet 26 of in-line connector 20 when extension catheter is inserted therethrough. As a further alternative, an end cap may have stopper portion having a length that extends substantially for the length of the lumen of second branch inlet 26, such that it prevents blood from pooling in the lumen of second branch inlet 26.

Referring now to FIG. 3B, end cap 34 includes adapter portion 35 that may be inserted into the outlet tubing of a conventional ECMO system. End cap 34 preferably includes internal lumen 36 having a diameter smaller than the lumen of second branch inlet 26, and suitable for, e.g., drug infusion or pressure/flow monitoring. Moreover, end cap 34 may include a hemostatic valve positioned within lumen 36 to prevent backflow of blood therethrough. As will be understood by a person of ordinary skill in the art, alternatively or in addition to a hemostatic valve, end cap 34 may include, e.g., a screw (aperture) valve, a balloon valve, a double membrane valve, etc. Alternatively, lumen 36 may have a diameter selected depending on which procedure is desired. End cap 34 may be coupled to a second arm of in-line connector 20 described above to permit delivery of interventional tools and/or removal of an existing ECMO cannula therethrough as described above. End cap 34 may be, e.g., a screw cap, that may be rotatably coupled to the in-line connector and/or existing ECMO cannula.

In accordance with another aspect of the present invention, end cap 34 may be incorporated directly into an existing ECMO cannula. For example, instead of use of an in-line connector to couple the existing ECMO cannula with the ECMO circuit, end cap 34 may be coupled to the existing ECMO cannula directly, e.g., either as two separate components coupled together or an integral component, such that the existing ECMO cannula is in fluid communication with the ECMO circuit via end cap 34. As described above, end cap 34 may include one or more hemostatic valves to prevent backflow of blood therethrough. If an existing ECMO cannula needs to be removed and/or replaced, e.g., to exchange an existing ECMO cannula for a larger diameter ECMO cannula, the existing ECMO cannula may be removed through the lumen of end cap 34.

For example, at the time an ECMO cannula needs to be removed, a clamp may be applied to the ECMO circuit so that the ECMO circuit may be decoupled from end cap 34. A guidewire then may be introduced through the lumen of end cap 34. The existing ECMO cannula may be removed over the guidewire, and a new, larger ECMO cannula, e.g., a 19 Fr cannula, may be advanced over the guidewire through the lumen of end cap 34, and positioned within the patient's vasculature. The ECMO circuit may then be recoupled to end cap 34 and unclamped to permit blood to once again flow from the ECMO circuit through the new, larger ECMO cannula. Similarly, the ECMO circuit may be decoupled from end cap 34 in the manner described above when interventional tool(s) need to be delivered to the patient, and recoupled when the interventional procedure is complete.

Figure 4A:
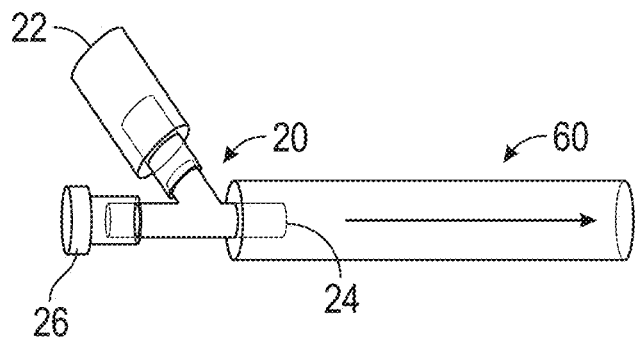
FIGS. 4A-4C are schematic views illustrating use of an exemplary in-line connector with an exemplary extension cannula in an ECMO system.
Figure 4B:
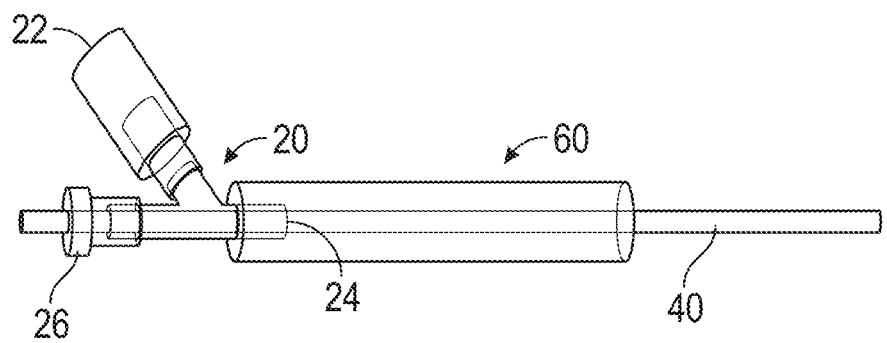
Figure 4C:
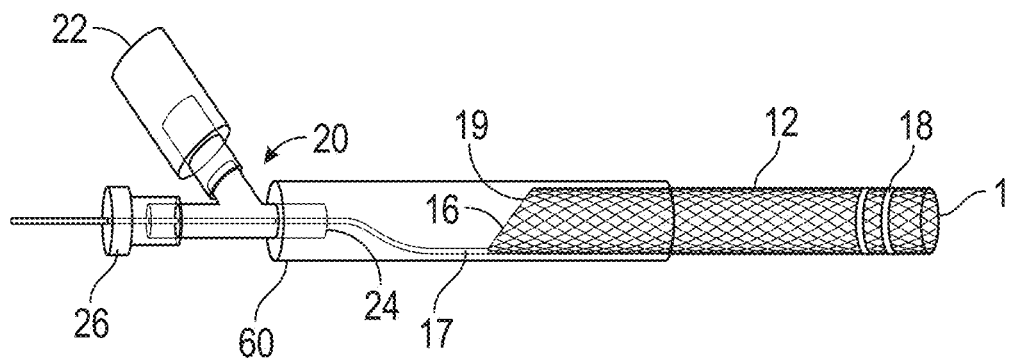

Referring now to FIGS. 4A to 4C, operation of the embodiment of the extension cannula of FIGS. 1A and 1B is schematically depicted in conjunction with in-line connector 20 of FIG. 3A. First, conventional ECMO cannula 60 is coupled to outlet 24 of in-line connector 20 and inserted into a patient's arterial vasculature, e.g., via a cut down to the femoral artery, as shown in FIG. 4A. The outlet line from an ECMO machine is coupled to first branch inlet 22. As shown in FIG. 4B, extension cannula 10, disposed with self-expanding conduit 12 in its collapsed insertion state within delivery sheath 40, is advanced through the hemostatic valve of second branch inlet 26 of in-line connector 20. Extension cannula 10 is positioned so that the distal end of self-expanding conduit 12 is disposed in the desired location, e.g., within the thoracic aorta, and the proximal end of self-expanding conduit 12 lies near the distal outlet of the conventional ECMO return catheter, e.g., as may be determined under fluoroscopy using, e.g., radiopaque marker bands disposed on sheath 40.

The lumen of sheath 40 preferably is dimensioned to accept and retain self-expanding conduit 12 in its collapsed insertion state. For example, the lumen of sheath 40 may have a diameter between 1.40 mm and 1.50 mm, and more preferably 1.45 mm. Sheath 40 has an outer diameter sized to it to be readily inserted through the lumen of a conventional VA-ECMO return cannula. Sheath 40 is slidably disposed over self-expanding conduit 12 so that it may be retracted relative to self-expanding conduit 12, thereby permitting self-expanding conduit 12 to self-expand from the collapsed insertion state to the expanded, deployed state.

Referring now to FIG. 4C, when sheath 40 and self-expanding conduit 12 are positioned in the desired location as described above, sheath 40 is retracted while self-expanding conduit 12 is held in position by elongated shaft 17 and handle 15, thereby permitting self-expanding conduit 12 to its expanded, deployed state. Because most of the length of self-expanding conduit 12 extends past the distal end conventional ECMO return cannula 60, oxygenated blood from the ECMO machine may be delivered to regions beyond those accessible with a conventional ECMO return cannula. In accordance with one aspect of the present invention, other interventional tools, e.g., vascular catheters, valve catheters, or intra-aortic or trans-valvular pumps, e.g., Impella® pump (made available by Abiomed, Danvers, Mass.), also may be inserted through the ECMO cannula via second branch inlet 26 of in-line connector 20 to perform additional interventional procedures simultaneously with VA-ECMO. Moreover, arterial repair tools may delivered to the patient's vasculature through the in-line connector to facilitate removal of, e.g., an arterial cannula. For example, the in-line connector may be used to provide wire re-access to the native femoral vessel, thereby allowing for removal of the ECMO cannula and delivery of vascular closure devices at the time of ECMO decannulation, thereby avoiding the need for surgical repair of the vessel.

In one preferred embodiment of extension cannula 10, self-expanding conduit 12 has a length between 30 to 40 cm or longer. In this manner, blood may be delivered in the vicinity of a patient's thoracic aorta, above the patient's renal artery ostia, to avoid high flow rates in the vicinity of the patient's renal arteries and reduce the risk of perfusion injury. In addition, if the distal end of self-expanding conduit 12 is disposed in the ascending aorta, as may be determined under fluoroscopy using radiopaque marker bands 18, outflow from self-expanding conduit 12 can provide oxygenated blood to the cardiac arteries in the vicinity of the aortic root and also provide antegrade flow to the carotid arteries and downstream arteries.

Still referring to FIG. 4C, when the patient is to be removed from ECMO, sheath 40 may be re-inserted over elongated shaft 17 and advanced to collapse and retrieve self-expanding conduit 12. In this case, sheath 40 will first engage tapered proximal end 19 of self-expanding conduit 12, such that advancement of sheath 40 while retaining shaft 17 stationary will cause self-expanding conduit 12 to collapse inward and return to its reduced diameter, collapsed insertion state. Extension cannula 10 and sheath 40 may then be removed through the hemostatic valve within second branch inlet 26. Use and operation of the embodiment of FIG. 2 is substantially the same as described above.

Figure 4D:
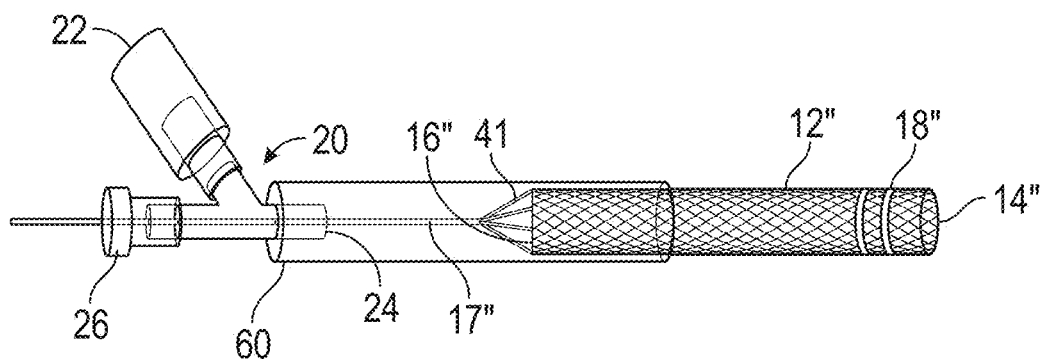
FIG. 4D is a schematic view illustrating use of an exemplary in-line connector with an alternative exemplary extension cannula in an ECMO system.

Referring now to FIG. 4D, a further alternative embodiment of an extension cannula and sheath constructed in accordance with the principles of the present invention is described. Self-expanding conduit 12" is constructed similar to self-expanding conduit 12 of FIG. 4C. For example, self-expanding conduit 12" has inlet 16", outlet 14", and one or more radiopaque marker bands 18", which correspond with inlet 16, outlet 14, and bands 18 of self-expanding conduit 12, respectively. Self-expanding conduit 12" differs from self-expanding conduit 12 in that, instead of tapered inlet geometry 19, self-expanding conduit 12" has plurality of angled legs 41 that couple self-expanding conduit 12" to elongated shaft 17" to facilitate resheathing for removal. Preferably, angled legs 41 are flexible and of uniform length, so that when the distal end of sheath 40 is advanced over angled legs 41, the legs flex inward to cause the support structure of self-expanding conduit 12" to collapse inward.

Moreover, sheath 40 may have a rapid exchange configuration, with sheath 40 having a length suitable for covering the entire length of self-expanding conduit 12, 12" but is joined to a support shaft and a handle coupled to the end of the support shaft. In this manner, sheath 40 may be back-loaded over the proximal end of elongated shaft 17 of the extension cannula and manipulated using the support shaft via the handle, without interfering with the ability to manipulate the proximal end of shaft 17.

Still referring to FIG. 4D, operation for the alternative embodiment of the extension cannula is similar to that of the embodiment of FIGS. 4A to 4C. As shown in FIG. 4D, self-expanding conduit 12" and sheath 40 are advanced through in-line connector 20 (see FIG. 2) and into the lumen of conventional ECMO return cannula 60 with self-expanding conduit 12" in the collapsed insertion state within sheath 40. Sheath 40 is withdrawn proximally while self-expanding conduit 12" is retained stationary using elongated shaft 17", thereby permitting self-expanding conduit 12" to self-expand to its predetermined diameter. Once sheath 40 is fully withdrawn, blood flow through conventional ECMO return catheter 60 is directed through angled legs 41 to the outlet of self-expanding conduit 12", which flex outward as the support structure of self-expanding conduit 12" self-expands. When the ECMO procedure is completed, blood flow from the ECMO machine is paused. Sheath 40 then is back-loaded over elongated shaft 17" of the extension cannula, and advanced distally using the support shaft of sheath 40 as described above. When the distal end of sheath 40 contacts angled legs 41, it causes the legs to flex inwardly and the proximal end of the support structure of self-expanding conduit 12" to transition to its insertion diameter. Accordingly, further distal advancement of sheath 40 causes the remaining length of self-expanding conduit 12" to transition to the collapsed insertion state, thereby facilitating removal of the extension cannula.

Figure 5:
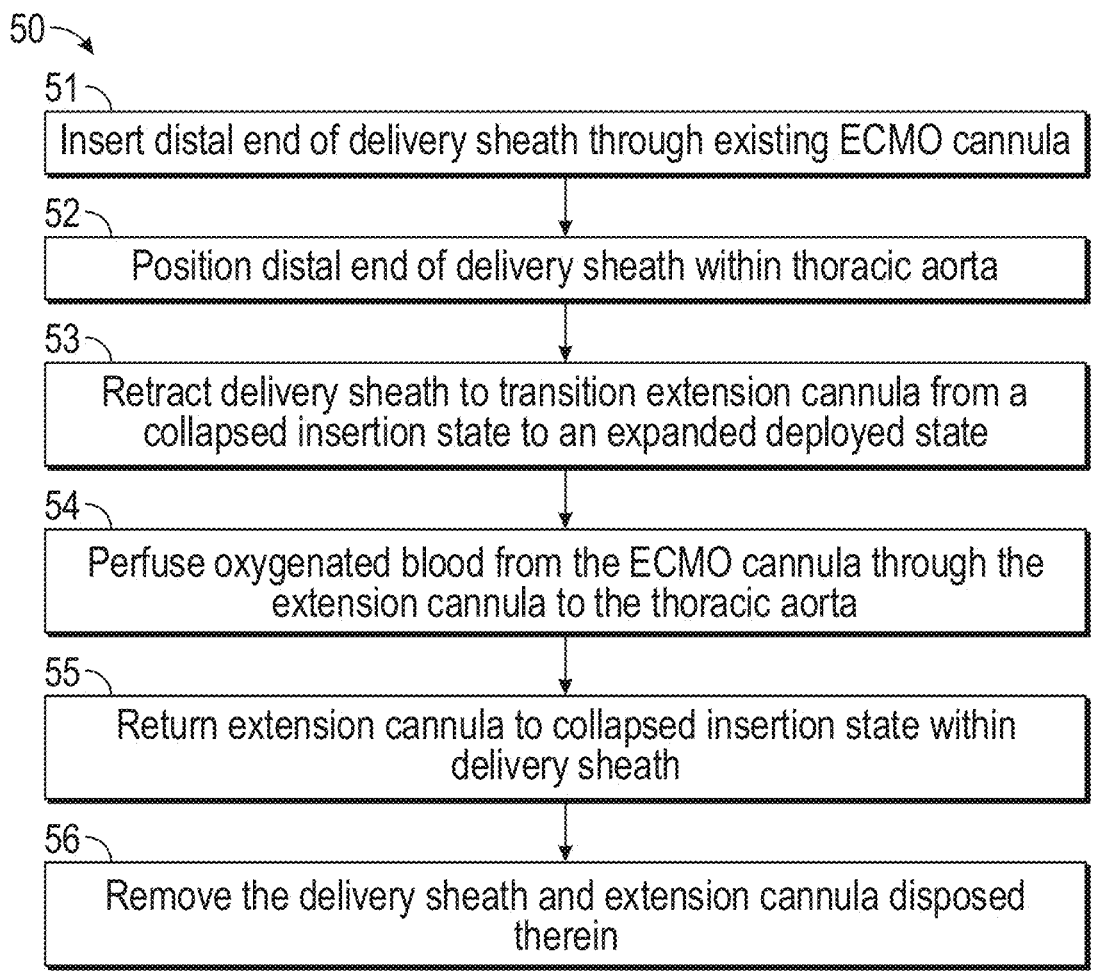
FIG. 5 is a flow chart of exemplary steps for improving perfusion during ECMO in accordance with the principles of the present invention.
Figure 6A:
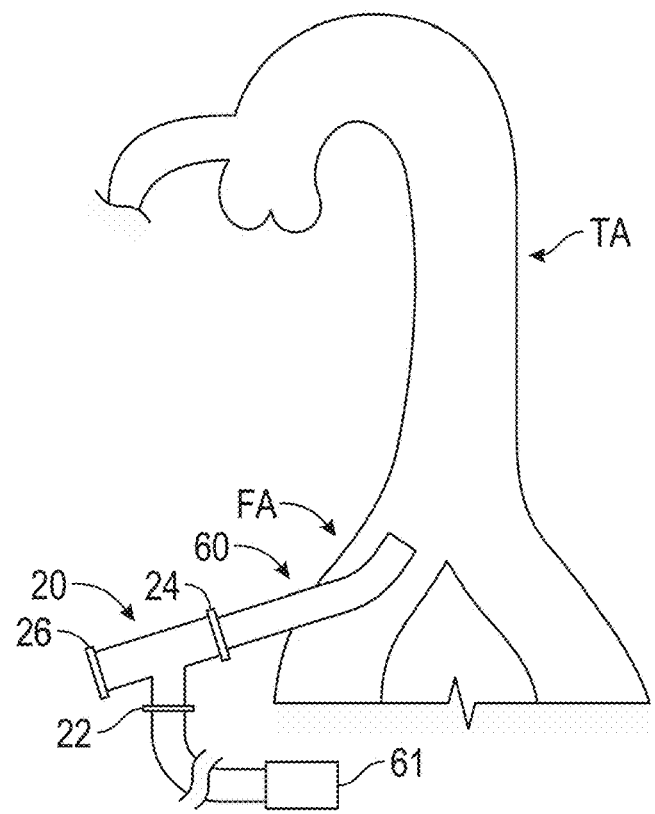
FIGS. 6A-6E illustrate the exemplary steps for improving perfusion during ECMO using the extension cannula of the present invention.
Figure 6B:
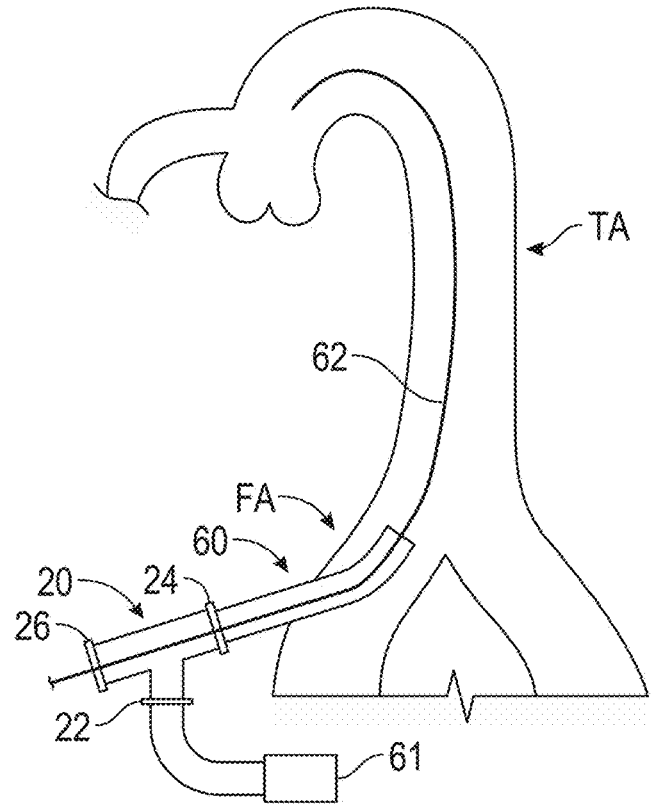

Referring now to FIG. 5, a flow chart of exemplary steps for improving perfusion during ECMO in accordance with the principles of the present invention is provided. Some of the steps of method 50 may be further elaborated by referring to FIGS. 6A to 6E. For example, FIG. 6A illustrates conventional ECMO cannula 60 inserted through the patient's femoral artery FA coupled to ECMO machine 61 via outlet 24 and first inlet 22 of in-line connector 20 as described above. As shown in FIG. 6B, guidewire 62 may be inserted through second branch inlet 26 and outlet 24 of in-line connector 20, and through ECMO cannula 60 until the distal end of guidewire 62 is advanced to the desired location within the patient's vasculature, e.g., within the thoracic aorta TA such as within the ascending aorta or in the vicinity of the aortic arch.

Figure 6C:
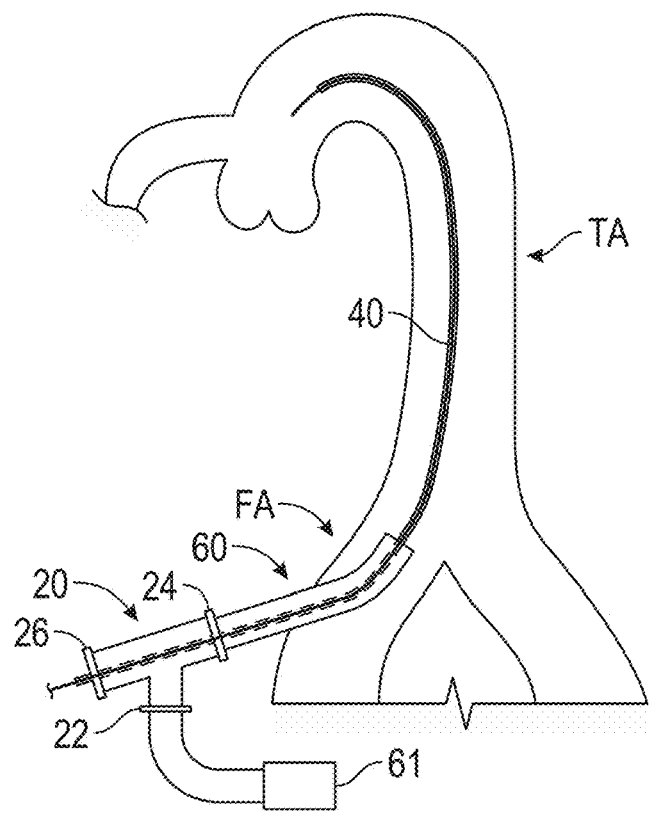
Figure 6D:
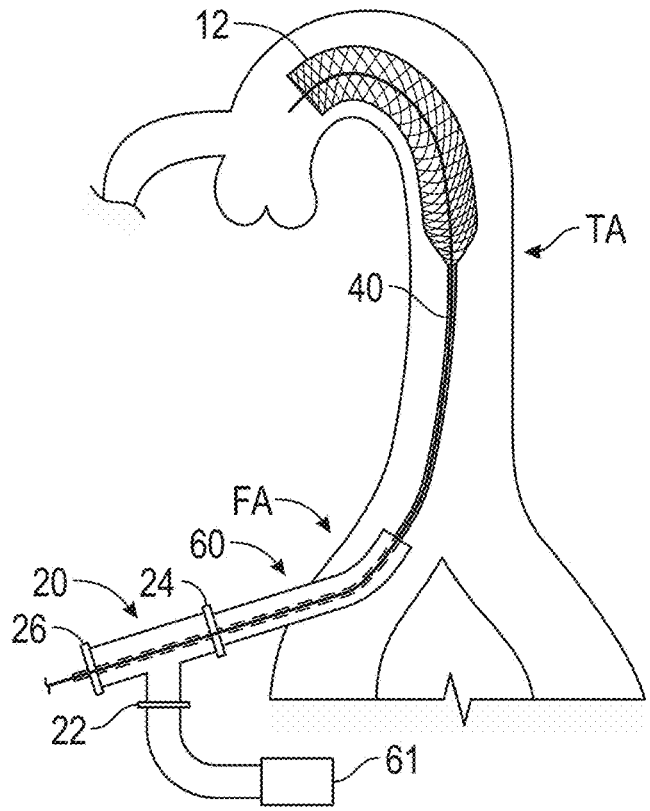
Figure 6E:
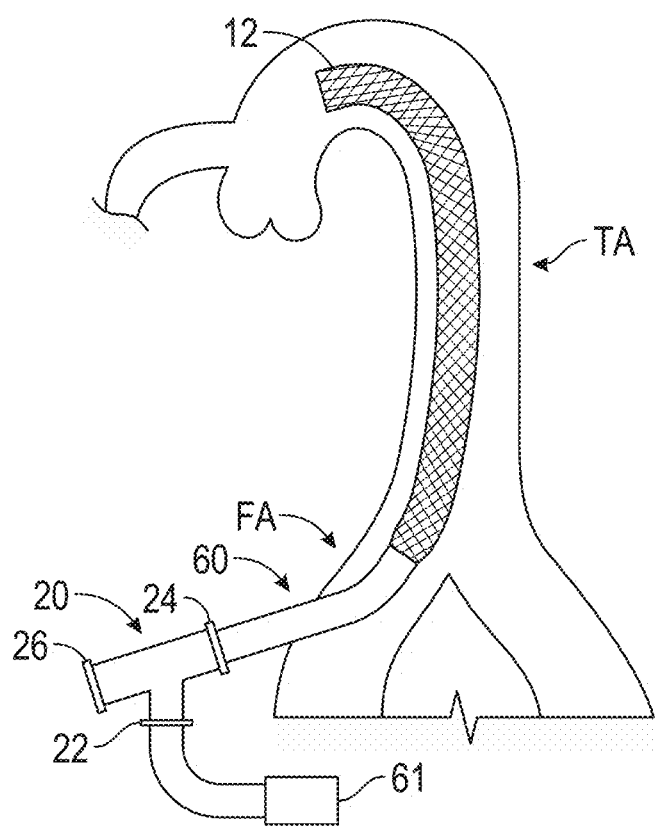

At step 51, the distal end of sheath 40, having self-expanding conduit 12 disposed therein in a collapsed insertion state, is advanced through ECMO cannula 60, e.g., over guidewire 62, via in-line connector 20. The distal end of sheath 40 advanced until it is positioned at the desired central location within the patient's vasculature at step 52 as shown in FIG. 6C. At step 53, sheath 40 is retracted relative to self-expanding conduit 12 slidably disposed within the lumen of sheath 40, while self-expanding conduit 12 remains stationary, causing self-expanding conduit 12 to transition from the collapsed insertion state to an expanded deployed state as shown in FIGS. 6D and 6E. FIG. 6D illustrates self-expanding conduit 12 partially fully expanded within the patient's vasculature, and FIG. 6E illustrates self-expanding conduit 12 fully expanded within the patient's vasculature, e.g., when self-expanding conduit 12 is fully exposed from sheath 40. Accordingly, at step 54, oxygenated blood may be perfused from ECMO cannula 60 to the central location within the patient's vasculature, e.g., within the ascending aorta or in the vicinity of the aortic arch. As a result, blood flow into the adjacent vessels, e.g., the coronary arteries and/or the carotid arteries, will occur and with a more normal antegrade flow pattern. As will be understood by a person of ordinary skill in the art, the outlet of self-expanding conduit 12 may be positioned within the descending aorta, e.g., the portion of the descending aorta approaching the level of the diaphragm from beneath the thoracic cavity or the portion of the descending aorta above the diaphragm.

In accordance with one aspect of the present invention, the ECMO pump may be programmed to generate a pulsatile flow to create pressure fluctuations at the outlet of self-expanding conduit 12 that mimics the patient's heartbeat. As a result, the patient may receive significant benefits such as retaining the elasticity of the arteries and reducing arterial stiffening, as opposed to with continuous flow. When the ECMO therapy is complete, at step 55, self-expanding conduit 12 may be returned to the collapsed insertion state within the lumen of sheath 40 as described above, and at step 56, sheath 40 and self-expanding conduit 12 disposed therein may be removed from the patient.

Figure 7:
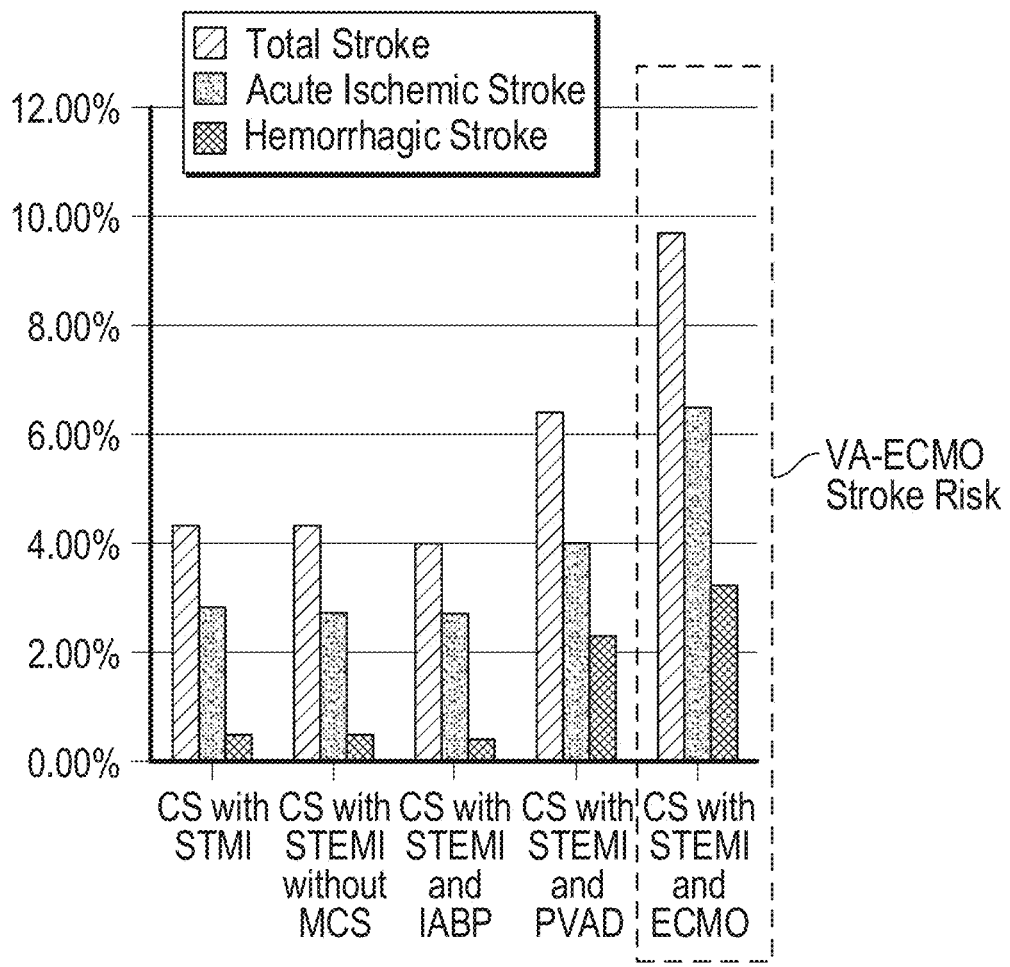
FIG. 7 is a graph illustrating VA-ECMO stroke risk.

FIG. 7 is a graph illustrating stroke risk for patient's undergoing various therapies include VA-ECMO. As shown, a patient undergoing VA-ECMO generally has the highest risk of total stroke, e.g., acute ischemic stroke and hemorrhagic stroke. In accordance with the principles of the present invention, the systems and methods described herein are expected to provide oxygenated blood to the cerebral vasculature and provide antegrade flow from the outlet of the self-expanding conduit. This in turn is expected to reduce the risk of ischemic stroke and reduce blood flow rates and pressures that could induce kidney injury.

Figure 8:
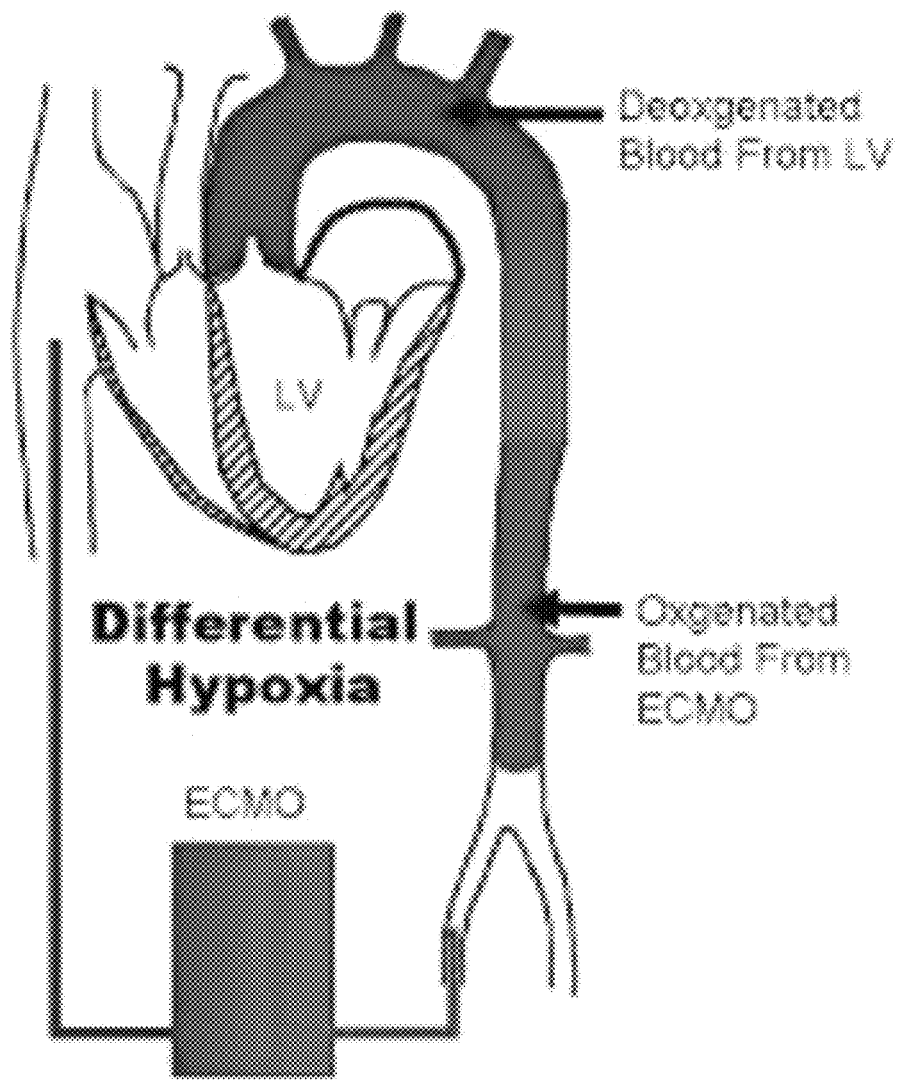
FIG. 8 depicts north-south syndrome in a patient on ECMO.

With respect to FIG. 8, a further expected benefit of the system and method of the present invention is described. FIG. 8 illustrates a situation referred to as "north-south syndrome" that may arise in a patient on ECMO, particularly patients having compromised lung function. In such cases, although the heat is beating, the blood returned to circulation by the left ventricle may be poorly oxygenated. In this case, if a conventional ECMO return catheter is employed, oxygenated blood reperfused into the patient mixes with the antegrade flow of deoxygenated blood from the lungs, resulting in differential hypoxia. Because the extension cannula of the present invention is designed to deliver blood into the ascending aorta, the system and methods of the present invention are expected to significantly ameliorate the effect of compromised lung function and reduce the occurrence and severity of north-south syndrome.

Figure 9:
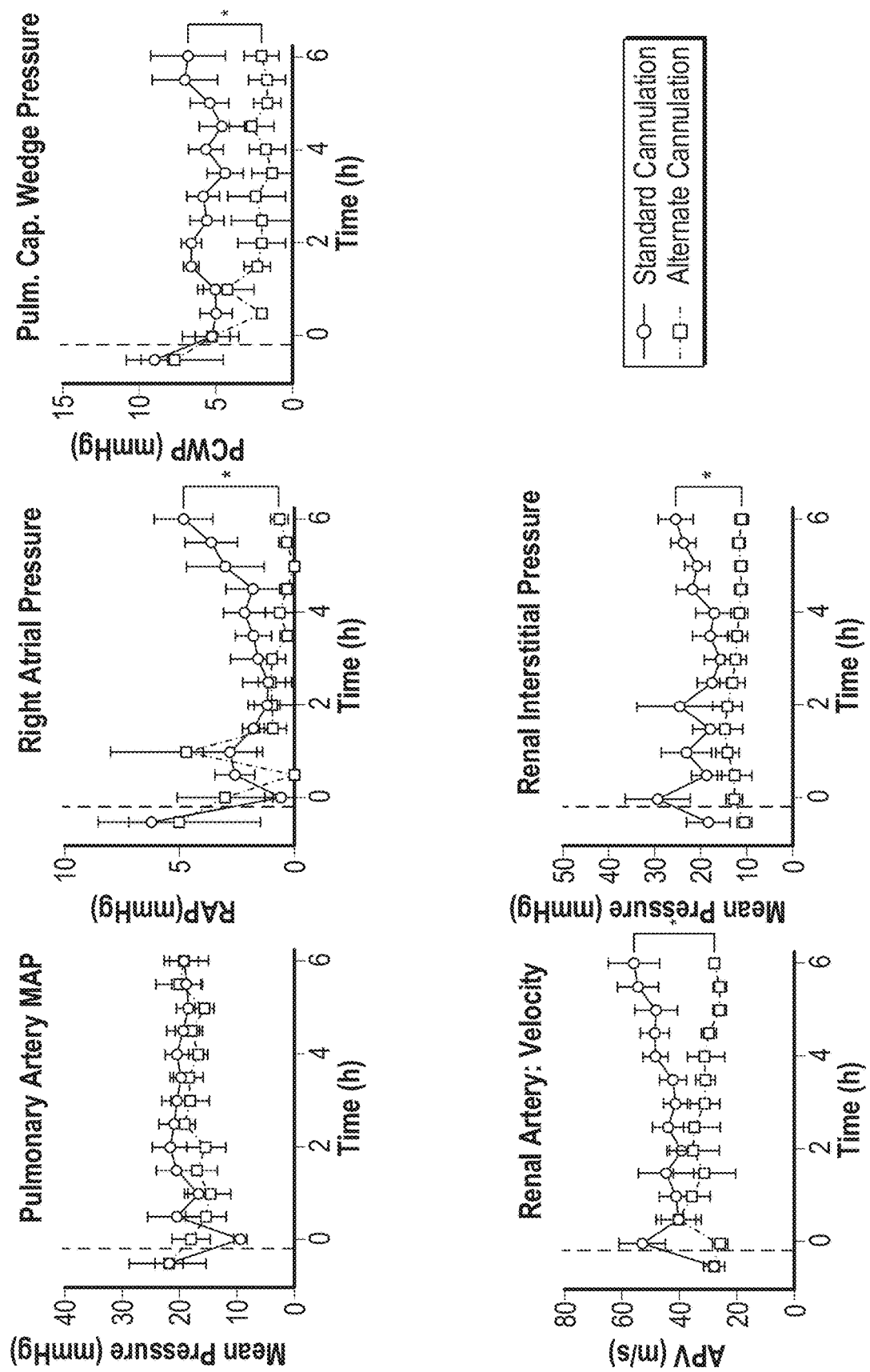
FIG. 9 is a series of graphs illustrating various parameters for standard conventional ECMO cannulation compared to those achieved using alternate cannulation (delivery of blood to the thoracic aorta) in accordance with the principles of the present invention.
Figure 10:
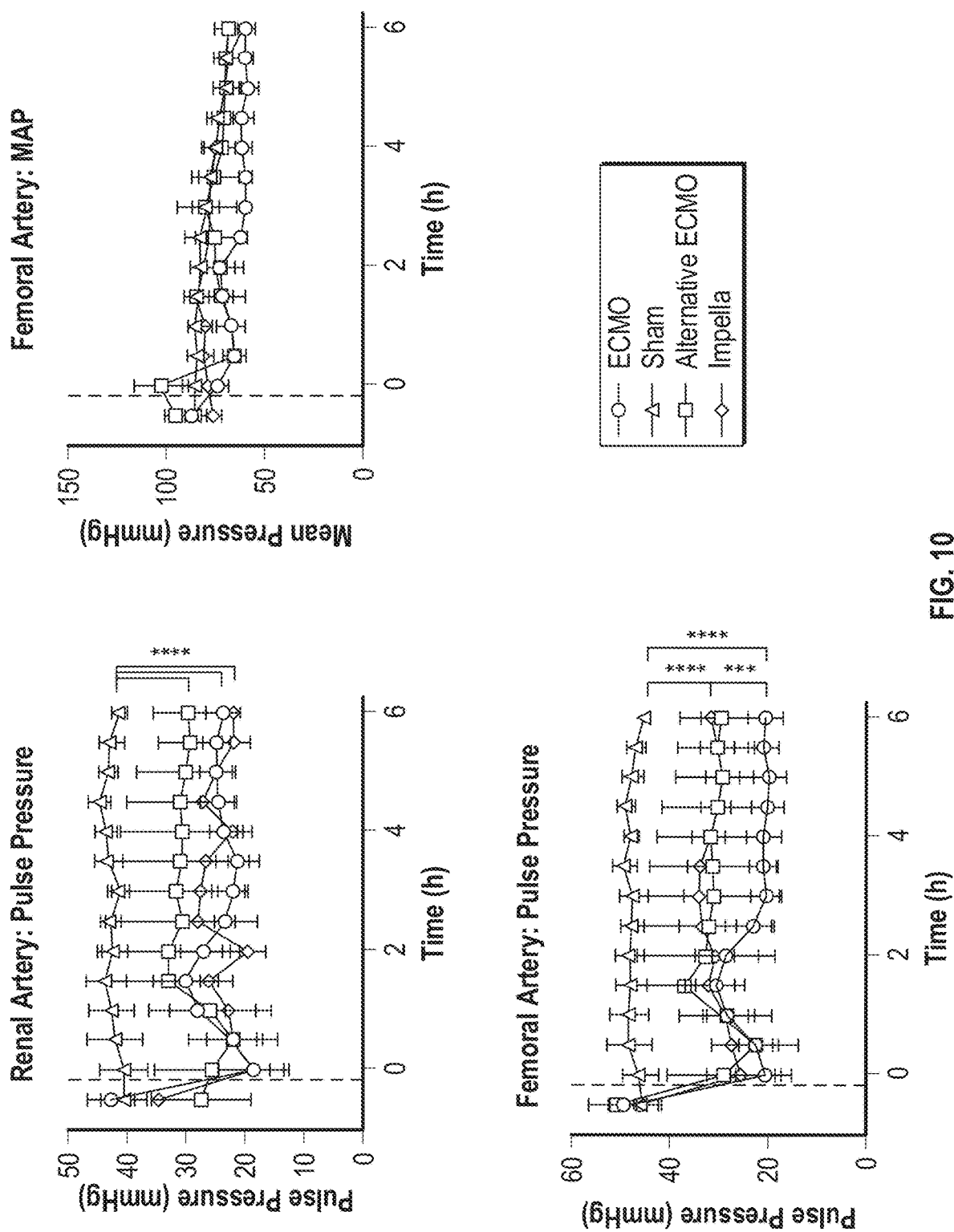
FIG. 10 is a series of graphs illustrating various parameters resulting from use of standard conventional ECMO cannulation, an Impella pump, and an exemplary system of the present invention.

Preclinical data from experiments utilizing an extension cannula constructed in accordance with the principles of the present invention demonstrate superior performance compared to conventional ECMO return cannulas. FIG. 9 is a series of graphs comparing various parameters measured during standard VA-ECMO cannulation and with use of the extension cannula of the present invention (defined as "Alternate Cannulation" in FIG. 9). In particular, the alternate cannulation of the present invention results in reduced pulmonary artery mean arterial pressure (MAP), reduced right arterial pressure, reduced pulmonary capillary wedge pressure, reduced renal arterial flow velocity, and reduced renal interstitial pressure (organ pressure), compared to standard VA-ECMO cannulation. These findings suggest that placement of an extension cannula may reduce cardiac, lung, and kidney injury when compared to standard VA-ECMO alone. Specifically, this data shows reduced heart pressures (right atrial pressure and pulmonary capillary wedge pressure), normal renal artery velocity, and normal renal interstitial (organ) pressures with alternate cannulation as opposed to standard cannulation (delivery of blood to the femoral artery). Further, as shown in FIG. 10, the alternate cannulation of the present invention provides increased pulsatile arterial flow in the renal artery and the femoral artery compared to standard VA-ECMO cannulation. Compared to sham operated animals, standard femoral cannulation ECMO reduces renal and femoral artery pulse pressure, e.g., pulsatility. Compared to standard cannulation, alternative cannulation (delivery of blood to the thoracic aorta) has increased renal and femoral artery pulse pressure, e.g., pulsatility. Improved physiologic pulsatility is further associated with less injury.

Figure 11:
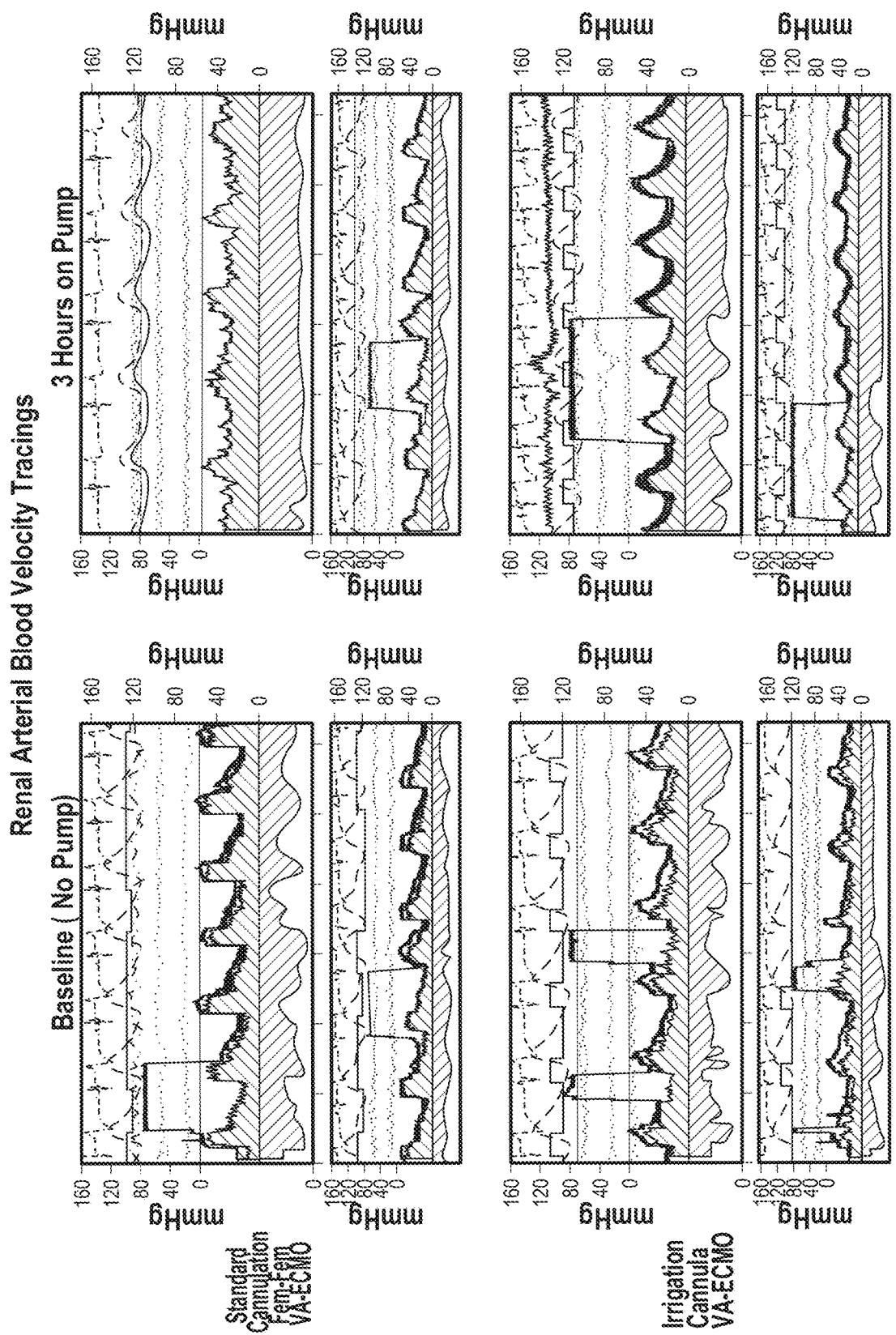
FIG. 11 is a series of graphs representing renal arterial blood velocity obtained for standard conventional ECMO cannulation and an exemplary alternate (irrigation) cannulation system of the present invention.
Figure 12:
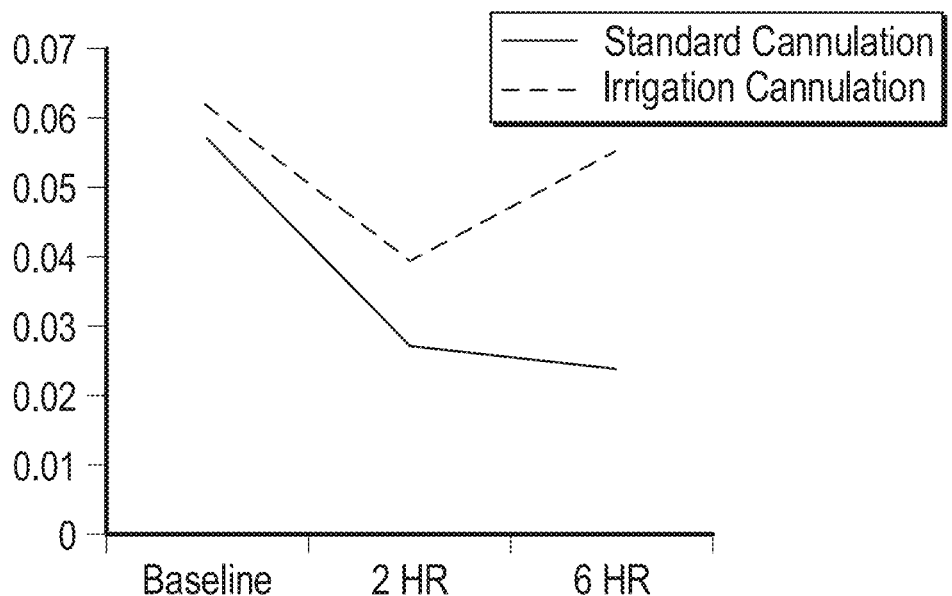
FIG. 12 are graphs illustrating renal arterial pulsatility and renal arterial microvascular resistance for standard conventional ECMO cannulation and an exemplary alternate cannulation system of the present invention.
Figure 12:
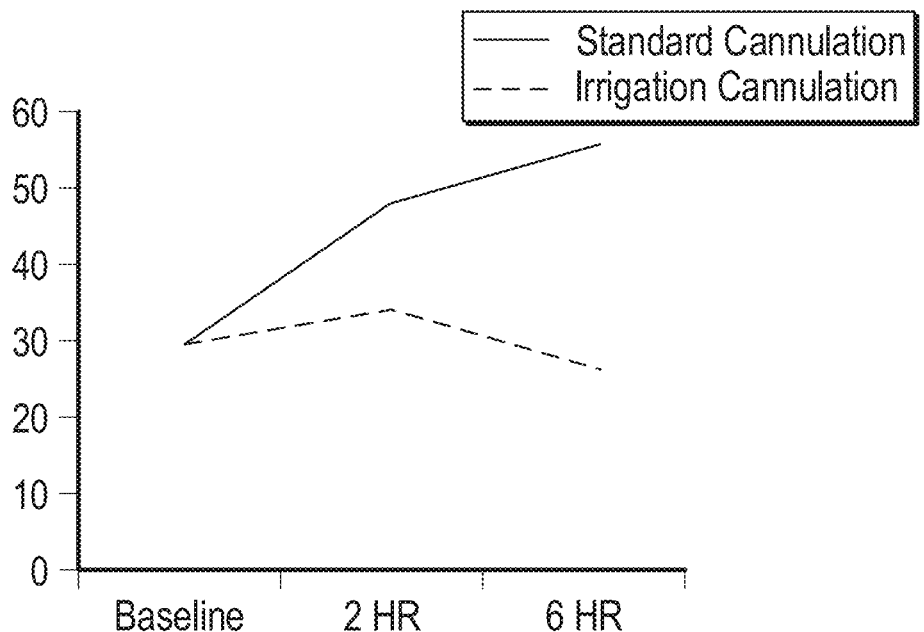
Figure 13:
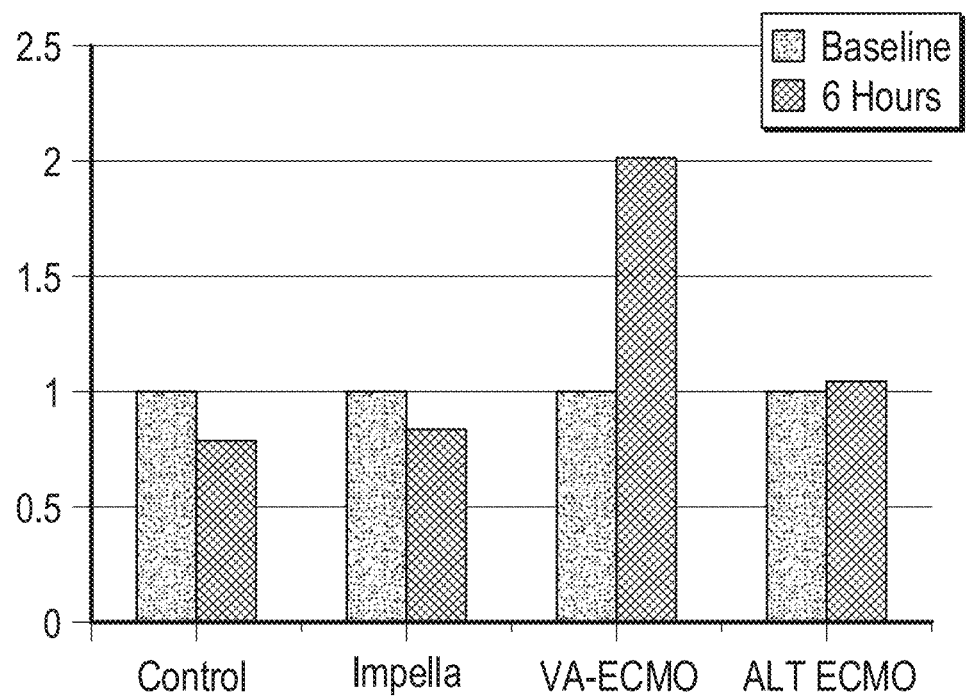
FIG. 13 is a graph showing urinary levels of kidney injury molecules associated with use of standard conventional ECMO cannulation and an exemplary alternate cannulation system of the present invention.

FIGS. 11 and 12 provide further comparisons of use of the alternate cannulation of the present invention compared to standard ECMO cannulation, demonstrating improved renal arty pulsatility and reduced microvascular resistance in the kidney. Regarding FIG. 11, compared to standard cannulation, alternate (irrigation) cannulation preserves pulsatility in the renal artery after three hours of pumping. Regarding FIG. 12, compared to standard cannulation, alternate (irrigation) cannulation preserves pulsatility (renal resistance index) and reduces renal arterial microvascular resistance in the renal artery after two and six hours of pumping. Similarly, FIG. 13 demonstrates that the alternate cannulation of the present invention ("ALT ECMO") results in lower levels of kidney injury molecule 1 (KIM-1) in the urine, indicating less kidney injury suffered by the patient. Compared to standard VA-ECMO, ALT ECMO is associated with lower (normal) levels of kidney injury marker in the urine.

While various illustrative embodiments of the invention are described above, it will be apparent to one skilled in the art that various changes and modifications may be made therein without departing from the invention. For example, as will be understood by a person having ordinary skill in the art, the systems and methods described herein are not limited for use with a VA-ECMO system. For example, the inventive extension cannula may also be used with, e.g., a venous-venous ECMO (VV-ECMO) system. Moreover, the extension cannulas and in-line connectors described herein may be used in conjunction with a conventional ECMO drainage catheter such that the extension cannula extends from the drainage catheter at the femoral vein to within the pulmonary artery or right ventricle of the patient, thereby permitting blood to be pumped directly out of the heart, effectively functioning as a ventricular assist device. The appended claims are intended to cover all such changes and modifications that fall within the true scope of the invention.

What is claimed:

1. An extension cannula for use with an ECMO return cannula having an inlet, an outlet and an internal diameter, a lumen of the ECMO return cannula configured to define a blood flow path extending from an ECMO machine to a location within a patient's vasculature proximal of a patient's renal vessels, the extension cannula comprising:

an elongated shaft having a proximal end and a distal region, the elongated shaft comprising a hypotube;

a conduit coupled to the distal region of the elongated shaft, the conduit having an inlet disposed in the distal region, an outlet and an internal lumen, the conduit configured to be inserted through the lumen of the ECMO return cannula in a collapsed insertion state and to transition between the collapsed insertion state and an expanded deployed state, the conduit biased to transition to the expanded deployed state to thereby form a continuation of the blood flow path through the lumen of the ECMO return cannula, the conduit in the expanded deployed state having a diameter equal to or greater than the internal diameter, wherein the elongated shaft is configured to permit the conduit to be advanced through the lumen of the ECMO return cannula to position the inlet of the conduit at a location within the outlet of the ECMO return cannula, and further configured so that the blood flow path does not pass through the elongated shaft, and wherein the conduit has a length selected so that when the extension cannula is inserted through the lumen of the ECMO return cannula, and transitioned to the expanded deployed state, the inlet of the conduit is positioned at the location within the outlet of the ECMO return cannula, proximal of the patient's renal vessels, and the outlet of the conduit extends beyond the outlet of the ECMO return cannula and the patient's renal vessels.

2. The extension cannula of claim 1, wherein the elongated shaft comprises stainless steel.

3. The extension cannula of claim 1, wherein the internal lumen of the conduit is configured to permit delivery of equipment used for coronary, peripheral vascular, cerebral intervention, or valve intervention, a catheter for antegrade limb perfusion, or for delivery of intra-aortic, trans-valvular pneumatic, or rotary flow pumps.

4. The extension cannula of claim 1, wherein the conduit comprises a support structure encapsulated with a flexible biocompatible coating.

5. The extension cannula of claim 4, wherein the support structure comprises a self-expanding mesh, weave or braid.

6. The extension cannula of claim 4, wherein the support structure comprises a shape-memory alloy, plastic or stainless steel.

7. The extension cannula of claim 4, further comprising a sheath configured to be removably disposed over the conduit to retain the conduit in the collapsed insertion state.

8. The extension cannula of claim 7, wherein the support structure in a vicinity of the inlet of the conduit comprises a feature that facilitates transition of the conduit to the collapsed insertion state when the sheath is advanced over the conduit.

9. The extension cannula of claim 8, wherein the feature comprises a tapered geometry of a proximal end of the support structure.

10. The extension cannula of claim 8, wherein the feature comprises a plurality of support legs that couple a proximal end of the support structure to the elongated shaft.

11. The extension cannula of claim 1, wherein the conduit comprises a soft, flexible material having one or more pores.

12. An extension cannula system comprising:
the extension cannula of claim 1; and
an in-line connector separate from the ECMO return cannula, the in-line connector having a first branch configured to be removably coupled to an outlet of an ECMO circuit, a second branch having a lumen configured to permit insertion of the extension cannula therethrough, and an outlet configured to be removably coupled to the ECMO return cannula, the first and second branches in fluid communication with the outlet of the in-line connector, wherein the second branch is co-linear with the outlet of the in-line connector.

13. An extension cannula for use with an ECMO return cannula having an inlet, an outlet and an internal diameter, an internal lumen that defines a blood flow path, the inlet configured to be coupled between an ECMO machine and the outlet configured to be disposed at a location within a patient's vasculature proximal of a patient's renal vessels, the extension cannula comprising:

a conduit having a proximal end, a distal end, a lumen extending therebetween, a length, a collapsed insertion state and an expanded deployed state, the conduit biased to transition from the collapsed insertion state to the expanded deployed state, the conduit in the expanded deployed state having a diameter equal to or greater than the internal diameter; and an elongated shaft having a distal region coupled to the conduit, the elongated shaft configured to advance the conduit in the collapsed insertion state through the internal lumen to position the proximal end within the outlet, the elongated shaft not forming part of the blood flow path, wherein the length of the conduit is selected so that when the proximal end is located within the outlet, disposed at the location within the patient's vasculature proximal of the patient's renal vessels, and the conduit is transitioned to the expanded deployed state, the lumen forms a continuation of the blood flow path through the internal lumen and the distal end extends beyond the patient's renal vessels.

14. The extension cannula of claim 13, wherein the elongated shaft comprises a hypotube.

15. The extension cannula of claim 13, wherein the elongated shaft comprises stainless steel.

16. The extension cannula of claim 13, wherein the lumen of the conduit is configured to permit delivery of equipment used for coronary, peripheral vascular, cerebral intervention, or valve intervention, a catheter for antegrade limb perfusion, or for delivery of intra-aortic, trans-valvular pneumatic, or rotary flow pumps.

17. The extension cannula of claim 13, wherein the conduit comprises a support structure.

18. The extension cannula of claim 17, wherein the conduit further comprises a flexible biocompatible coating disposed on the support structure.

19. The extension cannula of claim 17, wherein the support structure comprises a self-expanding mesh, weave or braid.

20. The extension cannula of claim 17, wherein the support structure comprises a shape-memory alloy, plastic or stainless steel.

21. The extension cannula of claim 13, further comprising a sheath configured to be removably disposed over the conduit to retain the conduit in the collapsed insertion state.

22. The extension cannula of claim 21, wherein the proximal end comprises a feature that facilitates transition of the conduit to the collapsed insertion state when the sheath is advanced over the conduit.

23. The extension cannula of claim 22, wherein the feature comprises a tapered geometry of the proximal end.

24. The extension cannula of claim 22, wherein the feature comprises a plurality of support legs that couple the proximal end to the elongated shaft.

25. The extension cannula of claim 13, wherein the conduit comprises a soft, flexible material having one or more pores.

26. An extension cannula system comprising:

the extension cannula of claim 13; and an in-line connector separate from the ECMO return cannula, the in-line connector having a first branch configured to be removably coupled to an outlet line from the ECMO machine, a second branch configured to permit insertion of the extension cannula therethrough, and a third branch configured to be removably coupled to the ECMO return cannula, the first and second branches in fluid communication with the third branch, wherein the second branch is co-linear with the third branch.

\* \* \* \* \*